(12) United States Patent
Bernstein

(10) Patent No.: US 7,740,590 B2
(45) Date of Patent: Jun. 22, 2010

(54) APPARATUS AND METHOD FOR DETERMINATION OF STROKE VOLUME USING THE BRACHIAL ARTERY

(75) Inventor: Donald P. Bernstein, Rancho Santa Fe, CA (US)

(73) Assignee: Cordeus, Inc., San Diego, CA (US)

( * ) Notice: Subject to any disclaimer, the term of this patent is extended or adjusted under 35 U.S.C. 154(b) by 0 days.

(21) Appl. No.: 12/489,335

(22) Filed: Jun. 22, 2009

(65) Prior Publication Data

US 2009/0259132 A1    Oct. 15, 2009

Related U.S. Application Data

(60) Division of application No. 11/158,521, filed on Jun. 21, 2005, which is a continuation-in-part of application No. 10/870,281, filed on Jun. 16, 2004, now Pat. No. 7,261,697.

(60) Provisional application No. 60/634,616, filed on Dec. 8, 2004.

(51) Int. Cl.
*A61B 5/02* (2006.01)

(52) U.S. Cl. .................. 600/506; 600/500; 600/501; 600/504; 600/513; 600/536

(58) Field of Classification Search ......... 600/500–501, 600/504, 506, 513, 536
See application file for complete search history.

(56) References Cited

U.S. PATENT DOCUMENTS

| | | | |
|---|---|---|---|
| 3,340,867 A | 9/1967 | Kubicek et al. | |
| 4,450,527 A | 5/1984 | Sramek | |
| 4,548,211 A | 10/1985 | Marks | |
| 4,562,843 A | 1/1986 | Djordjevich et al. | |
| 4,676,253 A | 6/1987 | Newman et al. | |
| 4,807,638 A | 2/1989 | Sramek | |

(Continued)

FOREIGN PATENT DOCUMENTS

EP    1304074 A2 *   4/2003

OTHER PUBLICATIONS

Moshkovitz Y., et al., Recent Developments in Cardiac Output Determination by Bioimpedance: Comparison with Invasive Cardiac Output and Potential Cardiovascular Applications, Current Opinion in Cardiology, 2004, 19:229-237.

(Continued)

*Primary Examiner*—Max Hindenburg
*Assistant Examiner*—Rene Towa
(74) *Attorney, Agent, or Firm*—DLA Piper LLP (US)

(57) ABSTRACT

Provided herein are methods and apparatus for stroke volume determination by bioimpedance from a patient's upper arm, or brachium, or a patient's thorax, utilizing pulsations of the arteries contained therein. The apparatus includes two or more spaced apart alternating current flow electrodes positioned on the patient's arm or thorax and two or more spaced apart voltage sensing electrodes positioned on the patient's arm or thorax and in-between alternating current flow electrodes. The system and method utilizes voltage sensed by the voltage sensing electrodes to calculate a cardiogenically induced impedance variation value of the patient, and to determine a stroke volume of the patient by multiplying the cardiogenically induced impedance variation value by a volume conductor $V_C$ and by a left ventricular ejection time $T_{LVE}$.

28 Claims, 5 Drawing Sheets

U.S. PATENT DOCUMENTS

| | | |
|---|---|---|
| 4,836,214 A | 6/1989 | Sramek |
| 4,953,556 A | 9/1990 | Evans |
| 5,103,828 A | 4/1992 | Sramek |
| 5,178,154 A | 1/1993 | Ackmann et al. |
| 5,309,917 A | 5/1994 | Wang et al. |
| 5,316,004 A | 5/1994 | Chesney et al. |
| 5,423,326 A | 6/1995 | Wang et al. |
| 5,469,859 A | 11/1995 | Tsoglin et al. |
| 5,503,157 A | 4/1996 | Sramek |
| 5,505,209 A | 4/1996 | Reining |
| 5,529,072 A | 6/1996 | Sramek |
| 5,685,316 A | 11/1997 | Schookin et al. |
| 5,782,774 A | 7/1998 | Shmulewitz |
| 5,791,349 A | 8/1998 | Shmulewitz |
| 6,016,445 A | 1/2000 | Baura |
| 6,058,325 A | 5/2000 | Baura |
| 6,095,987 A | 8/2000 | Shmulewitz et al. |
| 6,102,869 A | 8/2000 | Meier et al. |
| 6,161,038 A | 12/2000 | Schookin et al. |
| 6,186,955 B1 | 2/2001 | Baura |
| 6,511,438 B2 | 1/2003 | Bernstein et al. |
| 6,561,986 B2 | 5/2003 | Baura et al. |
| 6,602,201 B1 | 8/2003 | Hepp et al. |
| 6,636,754 B1 | 10/2003 | Baura et al. |
| 6,829,501 B2 | 12/2004 | Nielsen et al. |
| 2002/0193689 A1 | 12/2002 | Bernstein et al. |
| 2003/0163058 A1 | 8/2003 | Osypka et al. |

OTHER PUBLICATIONS

Wallace, Arthur W., et al., "Endotracheal Cardiac Output Monitor," Anesthesiology, vol. 92, pp. 178-189, Jan. 2000.

International Search Report and Written Opinion for International Application No. PCT/US05/20420 mailed on Sep. 25, 2006.

* cited by examiner

APPARATUS AND METHOD FOR DETERMINATION OF STROKE VOLUME USING THE BRACHIAL ARTERY

This Application is a divisional of U.S. patent application Ser. No. 11/158,521, filed on Jun. 21, 2005, which is continuation-in-part of U.S. application Ser. No. 10/870,281, filed Jun. 16, 2004 now U.S. Pat. No. 7,261,697, and claims priority from U.S. Provisional Patent Application No. 60/634,616, filed Dec. 8, 2004.

BACKGROUND OF THE INVENTION

1. Field of the Invention

This present invention relates to the determination of the volumetric output of the left ventricle of a person's heart per beat, known as stroke volume (SV) (mL), and, the volumetric output of a person's heart per minute, otherwise known as the cardiac output (CO) (L/Min). More particularly, this invention relates to the determination of SV and CO by transbrachial electrical bioimpedance.

2. Background Information

All methods, apparatus and inventions related to the measurement of SV/CO by the electrical bioimpedance method have heretofore been implemented either by the transthoracic method, also known as transthoracic or thoracic electrical bioimpedance plethysmography (or cardiography), or by total body (whole body) electrical bioimpedance plethysmography, also known as wholebody electrical bioimpedance cardiography (Moshkovitz Y, et al. Curr Opin Cardiol 2004; 19:229-237). Apart from a velocimetric method and apparatus described by Bernstein et al. (U.S. Pat. No. 6,511,438 B2), all prior art assumes a plethysmographic origin for the measured impedance change with respect to time ($\Delta Z(t)$), and its peak rate of change ($dZ/dt_{max}$), coinciding with each beat of the heart (Moshkovitz Y, et al. Curr Opin Cardiol 2004; 19:229-237). The plethysmograghic-based transthoracic SV equations used clinically basically comprise two methods; they are described in U.S. Pat. No. 6,511,438 B2, and are known as the Nyboer-Kubicek equation (Kubicek equation) and the Sramek-Bernstein equation. The deficiencies of the method and apparatus invented by Bernstein et al., disclosed in U.S. Pat. No. 6,511,438 B2, include the following:

1. A volume conductor, $V_c$, which underestimates the intrathoracic blood volume (ITBV) by approximately 15-20%
2. The implementation of a square root function for heart rate (H.R.) frequency (i.e. $\sqrt{f_0} = 1(T_{RR})^{0.5} = (H.R./60)^{0.5}$ which is superfluous and unnecessary.
3. A best method in the preferred embodiment for determining left ventricular ejection time, $T_{lve}$, is not disclosed.
4. A best method in the preferred embodiment for determining point B is not disclosed
5. A best method in the preferred embodiment for determining $dZ/dt_{max}$, based on the accurate determination of point B, is not disclosed There are numerous drawbacks to the current methods and apparatus used for measurement of the transthoracic electrical bioimpedance stroke volume parameters. What is needed is an alternative approach to the transthoracic electrical bioimpedance determination of stroke volume; specifically, an alternative site for signal acquisition, and better methods to measure the independent variables comprising the stroke volume equation.

SUMMARY OF THE INVENTION

An apparatus for determining stroke volume by bioimpedance from a patient that includes two or more spaced apart alternating current flow electrodes positionable on a patient, two or more spaced apart voltage sensing electrodes positionable on the patient and between the alternating current flow electrodes, an alternating current source electrically connected to the alternating current flow electrodes, a voltmeter electrically connected to the voltage sensing electrodes, and a processing unit in communication with the voltage sensing electrodes, wherein the processing unit is configured to use a voltage sensed by the voltage sensing electrodes to calculate a cardiogenically induced impedance variation value of the patient, and to determine a stroke volume of the patient by multiplying the cardiogenically induced impedance variation value by a volume conductor VC and by a left ventricular ejection time TLVE.

A method of determining stroke volume by bioimpedance from a patient including positioning two or more spaced apart alternating current flow electrodes on a patient, positioning two or more spaced apart voltage sensing electrodes on the patient and between the alternating current flow electrodes, providing an alternating current flow ($I(t)$) through the electrically conductive electrodes creating a current field, measuring a voltage ($U(t)$) between the voltage sensing electrodes within the current field, calculating a cardiogenically induced impedance variation value of the patient using the measured voltage ($U(t)$), and calculating a stroke volume of the patient by multiplying the cardiogenically induced impedance variation value by a volume conductor VC and by a left ventricular ejection time TLVE.

Other objects and features of the present invention will become apparent by a review of the specification, claims and appended figures.

BRIEF DESCRIPTION OF THE DRAWINGS

The drawings accompanying and forming part of this specification are included to depict certain aspects of the invention. A clearer conception of the invention, and of the components and operation of systems provided with the invention, will become more readily apparent by referring to the exemplary, and therefore nonlimiting, embodiments illustrated in the drawings, wherein identical reference numerals designate the same components. The invention may be better understood by reference to one or more of these drawings in combination with the description presented herein. It should be noted that the features illustrated in the drawings are not necessarily drawn to scale.

FIG. 3a further shows an example where points B and X are apparent on the dZ/dt curve and FIG. 3b shows an example where point B is not detectable, but point X is detectable on the dZ/dt curve.

DESCRIPTION OF PREFERRED EMBODIMENTS

Figure 1:
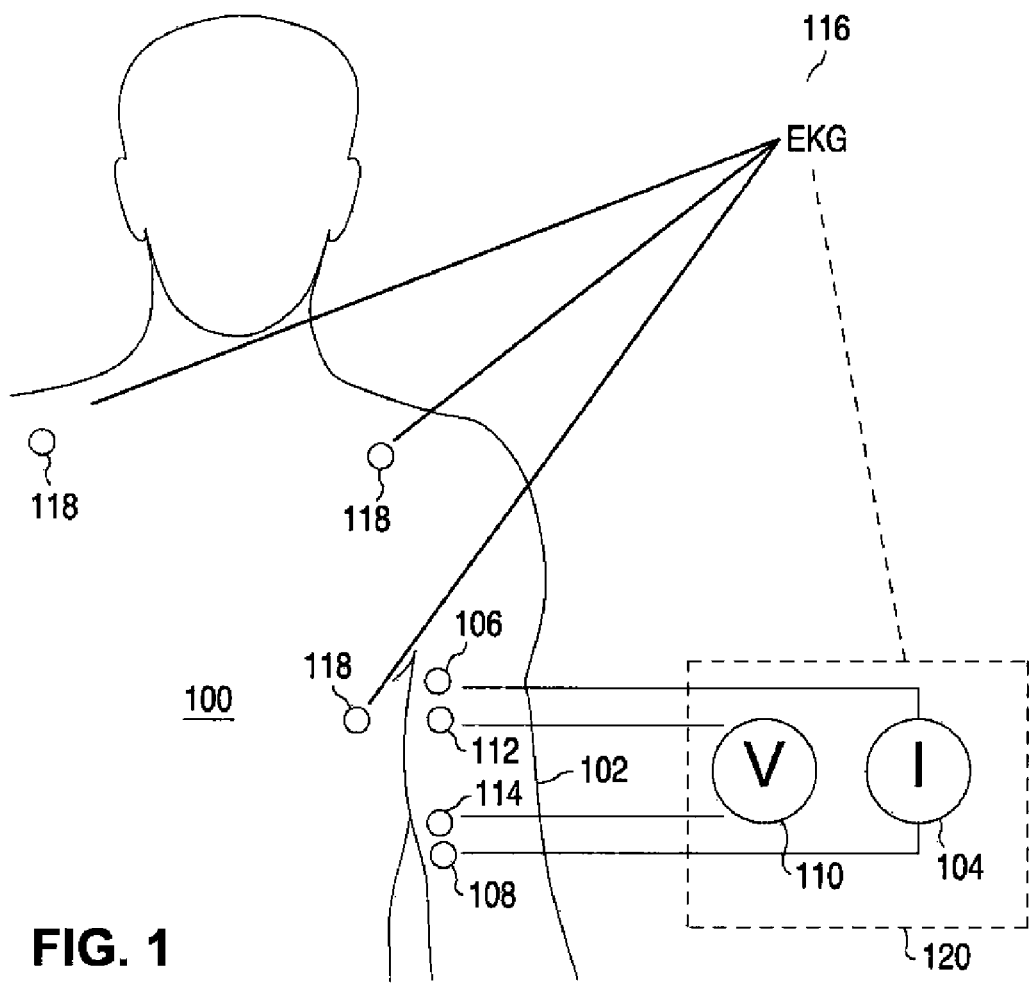
FIG. 1 shows placement of electrodes on a patient. A.C.(I) is injected through a segment of the upper arm, otherwise known as the brachium, the boundaries of which are the deltoid muscles of the shoulder and axilla proximally, and the elbow and antecubital fossa distally. Embedded within the brachial musculature and connective tissue, and anatomically situated medial to the brachial bone, otherwise known as the humerus, is the brachial artery. The upper arm, including the connective tissue, bone, nervous tissue, veins, and the brachial artery comprise an aggregate impedance (Z) to current flow. The passage of A.C across the brachium generates a quasi-static voltage, ($U_0$), and, concordant with every pressure pulse of the brachial artery, a time-dependent drop in voltage, ($\Delta U(t)$), this pressure pulse following every onset of left ventricular ejection with a short time delay.

The invention and the various features and advantageous details thereof are explained more fully with reference to the nonlimiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating preferred embodiments of the invention, are given by way of illustration only and not by way of limitation. Various substitutions, modifications, additions and/or rearrangements within the spirit and/or scope of the underlying inventive concept will become apparent to those skilled in the art from this disclosure.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of the "a" or "an" are employed to describe elements and components of the invention. This is done merely for convenience and to give a general sense of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The present invention discloses a method and apparatus for the determination of stroke volume (SV) and cardiac output (CO) by transbrachial electrical bioimpedance, wherein the signal source is the brachial artery. SV and CO, while not sensitive indices of the overall intrinsic force generation capacity, or contractility of the heart muscle, are the best indicators of the overall performance of the heart considered as a muscular pump. The apparatus and method disclosed involve the application of a constant magnitude alternating current of high frequency and small amplitude across a segment of a person's upper extremity, and more specifically, the upper arm, otherwise known as the brachium. The present invention may also provide for calibrating the transbrachial method and apparatus by determining SV/CO from the transthoracic approach. Thus, in contradistinction to the generally accepted transthoracic bioimpedance method for SV/CO determination, the present invention relates to the acquisition and signal processing of the cardiogenically-induced, pulsatile transbrachial bioimpedance signal for the purpose of SV/CO determination.

Advantages of the transbrachial method include:
1. Stroke volume (SV) and cardiac output (CO) values are not affected by excess, extra-vascular, intrathoracic liquids; namely, pulmonary edema fluid.
2. Baseline transbrachial quasi-static impedance, $Z_0$, is not affected by pulmonary (lung) ventilation, thereby obviating the necessity for sophisticated stabilizing adaptive filtering techniques to obtain a steady baseline for measurement of the cardiac-induced transbrachial impedance change, $\Delta Z(t)$, and the magnitudes and fiducial landmarks on its first time-derivative, transbrachial $dZ/dt$ and on its second time-derivative, $d^2Z/dt^2$.

3. The cumbersome and user-unfriendly transthoracic band, or tetrapolar spot-electrode array, is replaced by a circumferential or non-circumferential arm band or bands, an adhesive strip or other appropriate means for positioning the electrodes near the brachial artery containing a bipolar, or alternatively, a tetrapolar spot (or band) electrode array positioned on the medial aspect of the brachium between the axilla (arm pit) and a point distal on the brachium at the level of the olecranon process (elbow).

4. With the arm at rest, motion artifacts are minimized as compared to the transthoracic approach, and thus, adaptive filtering techniques are less critical.

5. Long-term monitoring of SV/CO in the surgical operating room, or intensive care unit, is facilitated by application of the apparatus to the arm, containing the bipolar, or, alternatively, the tetrapolar montage.

6. The bioimpedance signal obtained from the brachium is unaffected by the presence of chest thoracostomy tubes, external pacemaker wires, surgical bandages or appliances, and percutaneously placed central venous access catheters located in the neck or upper chest.

7. Without the perturbing influence of pulmonary ventilation, and pulmonary artery and other intrathoracic large vessel venous pulsations, the signal to noise ratio (S/N) relating to those portions the transbrachial $dZ/dt$ and $d^2Z/dt^2$ signals pertaining only to left ventricular ejection are substantially higher than that of the transthoracic approach.

Figure 7:
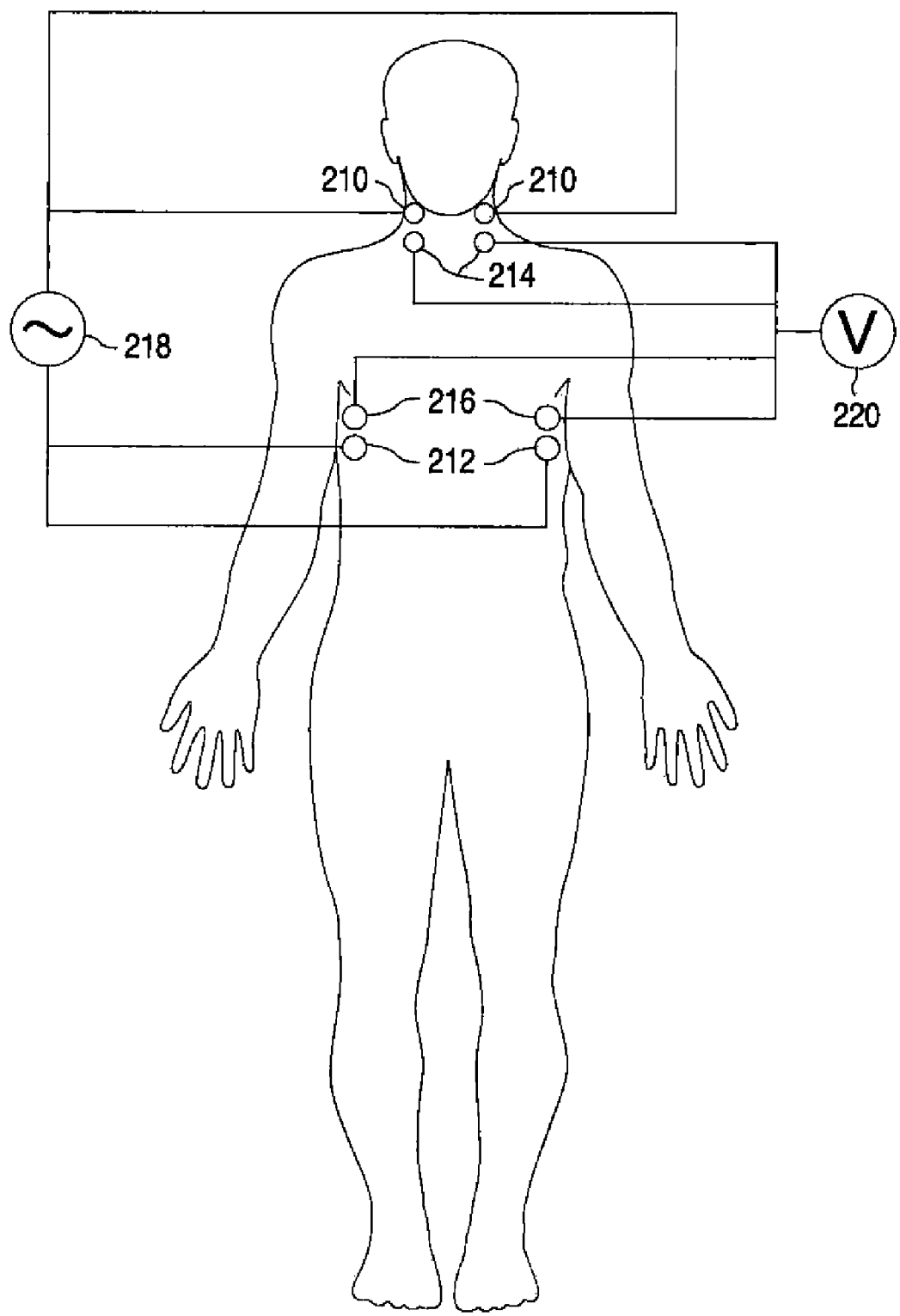
FIG. 7 shows placement of the electrodes on a patient implementing the transthoracic approach, which, as described herein, is required for calibration of the transbrachial approach if auto-calibration is not employed. As shown, A.C. (I) is injected through a segment of the thorax (chest) between the base of the neck (laterally) 210 and lower thorax (laterally) 212 at the level of the xiphoid process (inferior portion of the sternum, or breast bone) in the mid-axillary line. As operationally implemented, an A.C. field is applied to the thoracic volume between points 214 and 216, forcing an A.C. of high frequency (50-100 kH) and low magnitude (1.0-4.0 mA (rms)) to flow longitudinally between the neck and lower thorax. The A.C. causes, in the direction of the electrical field, and between the current injecting electrodes, a measured voltage, U(t). U(t) is further comprised of a static D.C. component, $U_0$, and a dynamic A.C. component, $\Delta U(t)$. The voltage, $U_0$, and voltage drop, $\Delta U(t)$, are sensed by electrodes proximate the current injecting electrodes, and within the current field. An A.C. generator 218 and voltmeter 220 are shown.

As disclosed above, the present invention relates to the measurement of stroke volume (SV) and cardiac output (CO) from the transbrachial method, using the brachial artery as the cardiogenically-induced signal source. Methodologically, the transbrachial method is similar to the transthoracic technique for determining SV. However, in the transthoracic technique, signal acquisition is effected over a segment of thorax by placement of voltage sensing electrodes 214 at the base of the neck, bilaterally, and voltage sensing electrodes 216 at the lower thorax at the xiphoid level, bilaterally (see FIG. 7). In contrast, the transbrachial technique uses a segment of brachium between voltage sensing electrodes 112/114 positioned proximate the axilla (arm pit) and junction of the upper and lower arm at the level of the olecranon process of the elbow. (see FIG. 1).

FIG. 1 schematically shows one apparatus embodiment according to the present invention, and its electrical interface with a subject 100. Signal acquisition from the upper arm 102 (brachium) requires application of a constant magnitude alternating current (A.C.) 104 of high frequency and small amplitude to electrodes 106, 108 that are spaced apart, with one or more electrodes affixed to the skin of the axilla, as well as one or more electrodes placed medially at the level of the antecubital fossa creating a current field. In this embodiment, the electrodes are applied to the subject's left arm. In other embodiments, the electrodes may be positioned on the right arm.

With the current field thus generated, the potential difference between the current injecting electrodes or alternating current flow electrodes 106, 108 is measured by a voltmeter 110 connected to the voltage sensing electrodes 112, 114 placed within the current field (see FIG. 1). A baseline impedance between the voltage sensing electrodes 112, 114, as well as a change in impedance, $\Delta Z(t)$ can be measured transbrachially. When the $\Delta Z(t)$ signal is electronically differentiated, $dZ/dt_{(brachium)}$ results, its peak systolic magnitude being $dZ/dt_{max(brachium)}$. For the purposes of the invention disclosed herein, $dZ/dt_{max}$ ($\Omega/s^2$) is equivalent to the nadir, or peak negative value of the rate of change of the impedance variation, $dZ/d_{min}$. It is also understood and stipulated that $-dZ/dt_{max}=+dZ/dt_{max}=dZ/dt_{min}$. When $dz/dt$ undergoes electronic differentiation, $d^2Z/dt^2_{(brachium)}$ ($\Omega/s^3$) results, its peak magnitude being $d^2Z/dt^2_{max(brachium)}$. For the purposes of the invention disclosed herein, $d^2Z/dt^2$ and $d^2Z/dt^2_{max}$ are equivalent to the rate of change and peak negative rate of change of $dZ/dt$ and $dZ/dt_{min}$, respectively. In the context of $dZ/dt_{max}$ being equivalent to $dZ/dt_{min}$, the interpretation of the peak magnitudes of their respective derivatives should be understood and furthermore stipulated as equivalent ($d^2Z/dt^2_{max}=d^2Z/dt^2_{min}$). Many different methods of applying the electrodes or electrode arrays to the arm are envisioned, such as spot electrodes, arm band(s) both circumferential and non-circumferential, adhesive strips or other attachment means known in the art. In one embodiment, an 8 spot-electrode array can be implemented. Alternatively, in another embodiment, a 4 spot-electrode array, placed on the inner, or medial aspect of the upper arm, proximate the brachial artery, can be implemented. Alternatively, 4 non-circumferential band (strip) electrodes, embedded in an adhesive carrier, may be affixed to the brachium, medially, and used in lieu of spot electrodes.

The voltages measured by the Voltmeter 110 not only contains a signal caused by the AC applied, but may also contain a signal component from which an electrocardiogram (ECG) can be derived. The application of filters separates the AC related and ECG related signal components. In another embodiment, EKG 116 may also be measured by placing EKG electrodes 118 on the patient 100. In the figure, a 3-lead EKG is shown and EKG is measured by known means. The magnitude of the alternating current (A.C.) 104 and voltmeter 110 may be components of an apparatus 120. The apparatus 120 may also include an input device and a processor. The input device may be any suitable device that provides information to the apparatus, such as a keyboard. The input device may also receive information from external sources, such as the EKG 116. The processor is in communication with the data input device, the alternating current source 104 and electrodes 106, 108, and the voltmeter 110 and electrodes 112, 114. The processor is configured to receive the information and calculae the stroke volume and cardiac output of the patient 100. The stroke volume and cardiac output of the patient may be displayed on a screen or be sent to other devices via a data output device of the apparatus.

Figure 2:
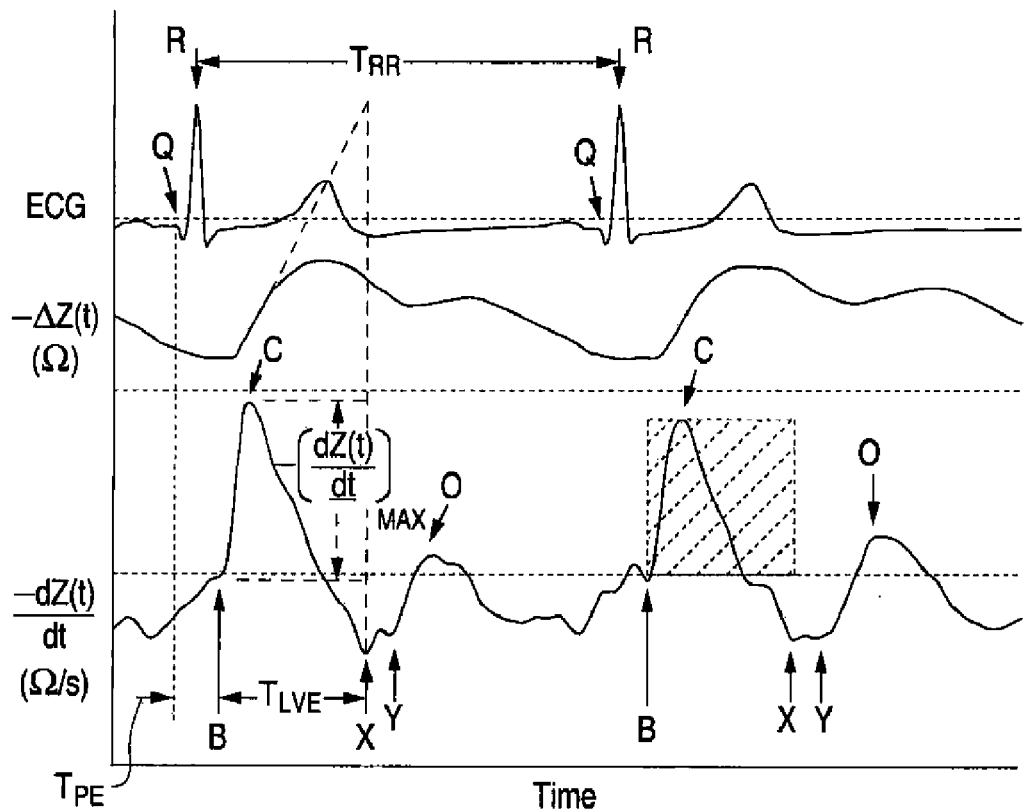
FIG. 2 shows an example of ECG, $\Delta Z(t)$ ($\Omega$) and $dZ/dt$ ($\Omega/s^2$) waveforms obtained transthoracically from a human subject, where $T_{RR}$=the R-R interval, or the time for one cardiac cycle (seconds, s); Q=onset of ventricular depolarization; ---------=maximum systolic upslope extrapolation of $\Delta Z(t)$; B=aortic valve opening; C=peak rate of change of the thoracic cardiogenic impedance variation, $dZ/dt_{max}$ ($\Omega/s^2$); X=aortic valve closure; Y=pulmonic valve closure; O=rapid ventricular filling wave; Q-B interval=pre-ejection period, $T_{PE}$ (seconds, s); B-C interval=time-to-peak dZ/dt, TTP (seconds, s); B-X interval=left ventricular ejection period, $T_{LVE}$ (seconds, s). dZ/dt waveform to the right shows $dZ/dt_{max}$ remaining constant throughout the ejection interval, $T_{LVE}$, which represents outflow compensation.

FIG. 2 shows an example of ECG, $\Delta Z(t)$ and $dZ/dt$ waveforms from a human subject 100, where $T_{RR}$=the R-R interval, or the time for one cardiac cycle; Q=onset of ventricular depolarization; ---------=maximum systolic upslope extrapolation of $\Delta Z(t)$; B=aortic valve opening; C=peak rate of change of the thoracic cardiogenic impedance variation, $dZ/dt_{max}$; X=aortic valve closure; Y=pulmonic valve closure; O=rapid ventricular filling wave; Q-B interval=pre-ejection period, $T_{PE}$; B-C interval=time-to-peak $dZ/dt$, TTP; B-X interval=left ventricular ejection period, $T_{LVE}$. $dZ/dt$ waveform to the right shows $dZ/dt_{max}$ remaining constant throughout the ejection interval, $T_{LVE}$.

Rationale for use of the brachium as an appropriate anatomic site for SV measurement by the bioimpedance technique is as follows. When A.C. (I) is injected through a segment of upper arm, otherwise known as the brachium, the boundaries of which are the deltoid muscles of the shoulder and axilla, proximally, and the elbow and antecubital fossa, distally, a quasi-static voltage, $U_0$, and voltage change, $\Delta U(t)$, can be measured between the current injecting electrodes. Embedded within the brachial musculature and connective tissue, and anatomically situated medial to the brachial bone, otherwise known as the humerus, is the brachial artery. The brachial artery is a large artery, continuous with both the subclavian and axillary arteries, and, whereas the left subclavian artery is a major branch of the arch of the thoracic aorta, the right subclavian artery is a branch of the brachiocephalic artery. The contents of the upper arm, including connective tissue, bone, nervous tissue, veins, and the brachial artery, comprise an impedance (Z) to current flow. The passage of A.C. across the brachium generates a quasi-static voltage, $U_0$, and, concordant with every pressure pulse of the brachial artery, a time-dependent drop in measured transbrachial voltage, $\Delta U(t)$, this following shortly after the onset of left ventricular ejection. The magnitude of the time delay ($\Delta t$, ms) between the brachial artery pressure pulse and the onset of left ventricular ejection is a function of pulse wave velocity. Transthoracically, the peak rate of change of impedance, $dZ/dt_{max}$, resulting from electronic differentiation of $\Delta Z(t)$, corresponds in time with peak aortic blood acceleration, $dv/dt_{max}$ (cm/s$^2$). Thus, in the preferred embodiment of the invention, $dZ/dt_{max(brachial)}$ represents the ohmic analog of peak blood acceleration in the brachial artery. Chemla et al. (Fundam Clin Pharmacol 1996; 10:393-399) showed that the measured acceleration of blood in the brachial artery is highly correlated (r=0.79) and linearly proportional with blood acceleration in the ascending aorta. Moreover, whereas the magnitude of brachial artery blood velocity is affected by downstream peripheral vasoactivity (vasodilation, vasoconstriction), the magnitude of brachial artery blood acceleration is modulated only by beta ($\beta$) adrenergic stimulation or depression of the cardiac adrenoceptors (Chemla D, et al. Am J Cardiol 1990; 65:494-500). As extrapolated from Visser (Ann Biomed Eng 1989; 17:463-463), when flowing blood is interrogated by a field of alternating current (A.C.), the acceleration of blood in the aorta is measured as the aortic reduced average blood acceleration which is the mean aortic acceleration divided by the vessel radius: $(dv/dt_{(mean)}/R$. When $[(dv/dt_{(mean)}/R]_{max}$, or peak aortic reduced average blood acceleration ($1/s^2$), undergoes square root transformation, peak aortic reduced average blood velocity (1/s) results. Likewise, when $dZ/dt_{max}/Z_0$ ($1/s^2$) undergoes square root transformation, ohmic mean velocity results, $\Delta Z_v(t)_{max}/Z_0$ (1/s). In the context of the present invention, where $dZ/dt_{max}$ represents ohmic mean acceleration, $dZ/dt_{max}/Z_0$ is herein referred to as the acceleration index (ACI). Because of the high correlation of $dv/dt_{max}$ measured in the aorta, with that of the brachial artery, it is claimed by the present invention that SV can also be obtained from the brachial artery. It has been discovered that processing the mean value of the second time-derivative of the impedance change provides results equivalent to processing the peak value of the first time-derivative, but with better accuracy. Thus, in the preferred embodiment, $$SV_{TB} = V_C \cdot \sqrt[3]{\left[\left(\frac{d^2Z/dt^2_{mean}}{Z_0}\right) \cdot 10^{-2}\right] \cdot T_{LVE}} \qquad \text{equation 1}$$

where $SV_{TB}$=transbrachial SV (mL); $V_{c(brachium)}$ equals the volume conductor (mL); $Z_0$ equals the quasi-static transbrachial base impedance (Ohm, $\Omega$); $T_{lve}$ equals left ventricular ejection time (s), and $d^2Z/dt^2_{mean}$ equals the mean value of the second time-derivative of the cardiogenically induced transbrachial impedance variation ($\Omega/s^3$). In a first embodiment:

$$d^2Z/dt^2_{mean}=(dZ/dt_{max})/TTP_m, \qquad \text{equation 1a}$$

where $TTP_m$=measured time to peak dZ/dt, defined as the temporal interval from point B to point C (seconds, s) in FIG. 2. In a second embodiment:

$$d^2Z/dt^2_{mean}=(dZ/dt_{max})/TTP_b, \qquad \text{equation 1b}$$

where 0.01 s$\leq TTP_b \leq$0.1 s, such as $TTP_b$=0.06 s. In a third embodiment:

$$d^2Z/dt^2_{mean}=(dZ/dt_{max})/TTP_c, \qquad \text{equation 1c}$$

where $TTP_c$=corrected rise time, or time to peak dZ/dt, which is the corrected temporal interval from point B to point C (s). Here, $TTP_c=(10^{-a})\times[1/(ACI)^b]$=s; where $[1/(ACI)^b]=ACI^{-b}$; "a" is a negative exponent such as 0>a$\geq$-5 or even a=-2; ACI=acceleration index=$dZ/dt_{max}/Z_0=1/s^2$; "b" is an exponent such as 0.1$\leq$b$\leq$1.0 or even b=0.5; where -b (minus b) is a negative exponent such as 0>-b$\geq$-10 or even -b (minus b)=-0.5; and 0.01 s$\leq TTP_c \leq$0.1 s. For example, in a preferred embodiment, $TTP_c=(10^{-2})\times[1/(ACI)^{0.5}]$=s. In a fourth embodiment:

$$d^2Z/dt^2_{mean}=dZ/dt_{max}/TTP_d, \qquad \text{equation 1d}$$

where $TTP_d(s)=(TTP_c+TTP_m)/A$; and 0<A$\leq$5 such as A=2; and 0.01 s$\leq TTP_d \leq$0.1 s. In a fifth embodiment:

$$d^2Z/dt^2_{mean}=dZ/dt_{max}/TTP_e, \qquad \text{equation 1e}$$

where $TTP_e(s)=(TTP_c+TTP_b)/A$; and 0<A$\leq$5 such as A=2; and 0.01 s$\leq TTP_e \leq$0.1 s. In a sixth embodiment:

$$d^2Z/dt^2_{mean}=dZ/dt_{max}/TTP_f, \qquad \text{equation 1f}$$

where $TTP_f=(TTP_m+TTP_b)/A$; and 0<A$\leq$5 such as A=2; and 0.01 s$\leq TTP_f \leq$0.1 s. In a seventh embodiment:

$$d^2Z/dt^2_{mean}=d^2Z/dt^2_{max}/B; \qquad \text{equation 1g}$$

where $d^2Z/dt^2_{max}$ ($\Omega/s^3$)=the maximal systolic upslope extrapolation of dZ/dt, peak first time-derivative of dZ/dt, or systolic peak rate of change of dZ/dt; and 0<B$\leq$10 such as B=2.

In one exemplary embodiment:
$V_{c(brachium)}=C_1 \cdot [W \cdot C_2]$;
$C_1=0<C_1 \leq 50,000$,
W=weight in kilograms (kg)
$C_2=C_3/(BMI_n)^y$
$BMI_n=BMI_p/C_4$ a. 35$\leq C_3 \leq$100 (mL/kg), wherein $C_3$ in the preferred embodiment=70 mL/kg;

b. $BMI_n$=normalized body mass index (dimensionless), wherein 0.5$\leq BMI_n \leq$4.0, wherein the preferred embodiment, $BMI_n$=1 c. $BMI_p$=a person's body mass index=Weight (kg)/Height (meters)$^2$ (kg/m$^2$) where W=a person's weight (kg), and H=a person's height (m).

d. 15$\leq C_4 \leq$40 kg/m$^2$, wherein $C_4$=ideal body mass index=24 kg/m$^2$ in the preferred embodiment.

e. 0.25$\leq$y$\leq$1.0, wherein y=0.5 in the preferred embodiment.

f. 35$\leq C_2 \leq$100, wherein the preferred embodiment, $C_2$=70 mL/kg

Unlike previously described bioimpedance techniques, which broadly assume a plethysmographic or volumetric origin for the cardiogenic impedance change, $\Delta Z(t)$, and its peak first time derivative, $dZ(t)/dt_{max}$, the present technique assumes $dZ(t)/dt_{max}$ to represent the ohmic equivalent of the peak acceleration of red blood cells. Thus, when the first time-derivative of $\Delta Z(t)$ is taken, $dZ/dt$, its peak magnitude, $dZ/dt_{max}$, can be shown to coincide in time with the peak red blood cell acceleration, $dv/dt_{max}$ (cm/s$^2$), and not with the peak rate of change of volume, $dV/dt_{max}$ (mL/s). Consequently, to obtain ohmic mean velocity, $dZ/dt_{max}/Z_0$ (1/s$^2$) must undergo square root transformation. This transformation is to be known as square root Acceleration Step-down Transformation: $\sqrt{[(dZ/dt_{max})/Z_0]}$ (1/s). It can also be shown that the cube root of the normalized mean value of the second time-derivative of the impedance change times $10^{-2}$, that is, $[(d^2Z/dt^2_{mean}/Z_0) \times 10^{-2}]^{0.333}$, yields ohmic mean velocity equivalent to the taking the square root of the peak value of the first time-derivative. Signal processing the mean value of the second time-derivative of $\Delta Z(t)$ has certain advantages over processing the first time-derivative (e.g. time to peak values calculated more accurately because of using cube root calculations over square root calculations), which are provided in another preferred embodiment using the transthoracic approach. To obtain brachial artery ohmic mean velocity, the cube root transformation is thus implemented in the preferred embodiment. Thus, the signal processing technique, comprising part of the invention, implies that the proper designation for the transbrachial approach is correctly stated as Transbrachial Electrical Bioimpedance Cardiovelocimetry or, simply, Transbrachial bioimpedance velocimetry.

Impedance Measurement Techniques in the Preferred Embodiment of the Invention

Figure 3A:
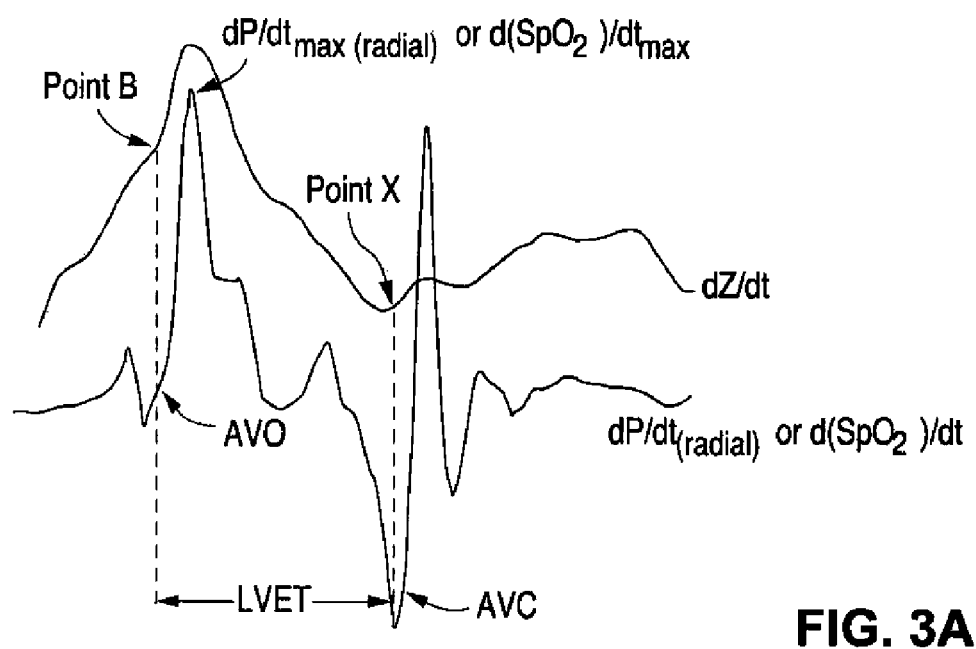
FIGS. 3a and 3b show the relationship between the dZ/dt curve and the dP/dt or $d(SpO_2)/dt$ curve.
Figure 3B:
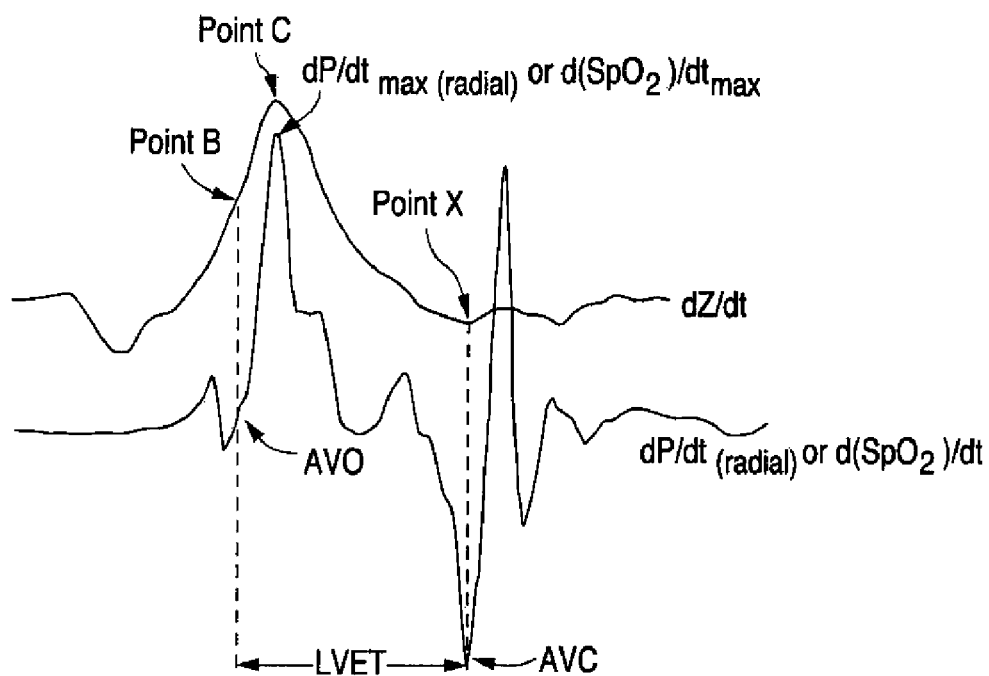

FIGS. 3a and 3b show the relationship between the $dZ/dt$ curve and either the $dP/dt$ or $d(SpO_2)/dt$ curves. FIG. 3a further shows an example where points B and X are apparent on the $dZ/dt$ curve and FIG. 3b shows an example where point B is not detectable, but point X is detectable on the $dz/dt$ curve. Thus, determination of left ventricular ejection time, ($T_{lve}$), onset of flow (point B), and the ohmic equivalent of peak brachial artery reduced average blood acceleration, ($dZ/dt_{max}/Z_{0(brachium)}$), while ideally measured directly from the $dZ/dt$ curve, are supplemented obligatorily by alternative means. The said alternative/obligatory means for determining $T_{lve}$ are those obtained from means such as from the waveform corresponding to the photoplethysmographic pulse oximetry waveform, $\Delta SpO_2(t)$, or its first time-derivative, $d(SpO_2)/dt$, and/or by the waveform obtained from a non-invasive applanated radial arterial pressure pulse waveform, $\Delta P(t)_{(radial)}$, or its first time-derivative, $dP/dt_{(radial)}$. (see FIG. 4)

The said means for determining point B on the transbrachial $dZ/dt$ curve are those methods used for determining $T_{lve}$ when point X on the transbrachial $dZ/dt$ curve, or its first time derivative ($d^2Z/dt^2$), are identifiable by those skilled in the art of bioimpedance curve analysis. When point X is not identifiable on the transbrachial $dZ/dt$ curve, or its first time-derivative, $d^2Z/dt^2$, then alternative means for point B detection are necessary. In the absence of an identifiable point X by those skilled in the art of $dZ/dt$ curve analysis, said means for point B detection include use of the first time-derivative of the applanated radial pressure waveform tracing, $dP/dt_{(radial)}$. It will be clear to those skilled in the art of curve analysis, why the aforementioned said means are superior to those disclosed by others, and most recently by Baura et al. (U.S. Pat. No. 6,561,986 B2).

Methods for Determination of Left Ventricular Ejection Time ($T_{lve}$, LVET):

1. $dZ/dt$ waveform analysis: $T_{lve}$ (LVET) measured across the brachium is defined as the temporal interval from point B, which corresponds to aortic valve opening (AVO), albeit with a time delay, to point X, which coincides in time, albeit with a short time delay, to aortic valve closure (AVC), these time delays dictated by pulse wave velocity.

Figure 8:
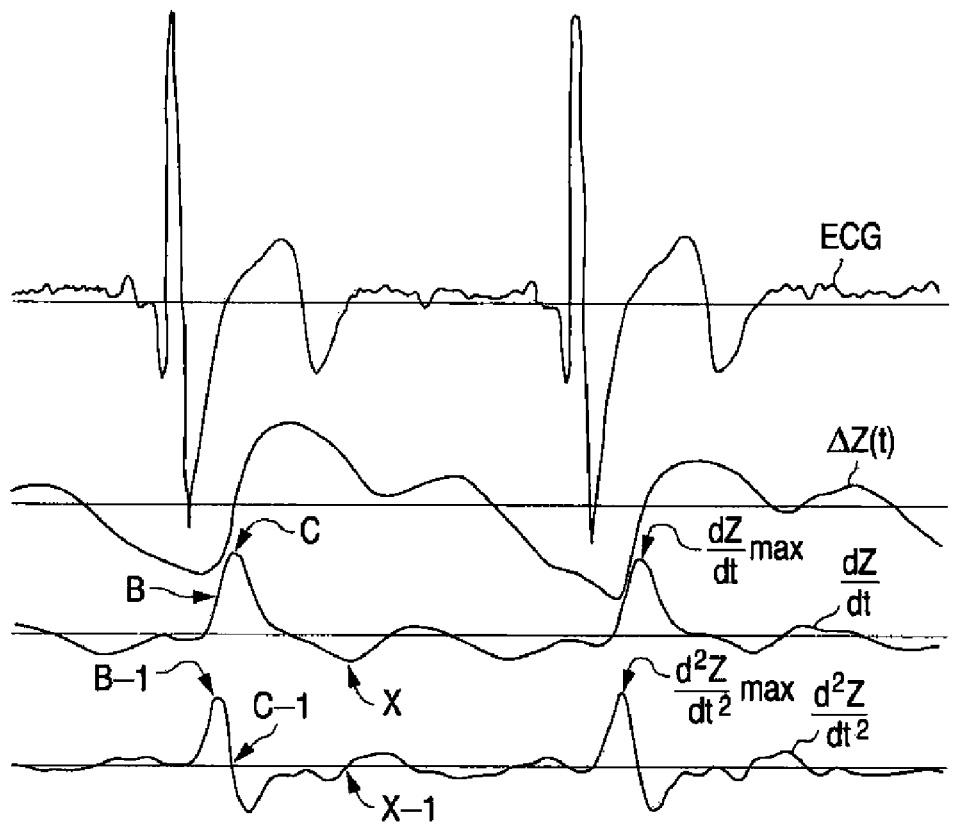
FIG. 8 shows waveform examples of the following: ECG, $\Delta Z(t)$, dZ/dt, and $d^2Z/dt^2$ ($\Omega/s^3$) from the transthoracic approach. Fiducial landmarks noted on the dZ/dt waveform are point B, denoting aortic valve opening, point C, denoting $dZ/dt_{max}$, and point X, denoting aortic valve closure. Fiducial landmarks noted on the $d^2Z/dt^2$ waveform are point B-1 indicating $d^2Z/dt^2_{max}$ and corresponding proximate in time to aortic valve opening; point C-1 corresponding to the first zero crossing and thus $dZ/dt_{max}$; and point X-1, corresponding to the second zero crossing and aortic valve closure (point X on the dZ/dt waveform). The magnitude, $d^2Z/dt^2_{max}$, is noted.

2. $d^2Z/dt^2$ waveform analysis: $T_{LVE}$ (LVET) measured from the peak second time-derivative of the transbrachial or transthoracic impedance pulse variation is defined as the temporal interval proximate the peak of the earliest positive systolic deflection of $d^2Z/dt^2$ (i.e. $d^2Z/dt^2_{max}$), corresponding proximate in time with point B on the $dZ/dt$ curve and the nadir of the rising foot of $\Delta Z(t)$, to, in the usual case, the second zero baseline impedance crossing of $d^2Z/dt^2$. To the ejection interval just described, 20 ms (i.e. 0.02 seconds) should be added. The second Zero crossing, following the first zero crossing corresponding to point C ($dZ/dt_{max}$), corresponds temporally with point X on the $dZ/dt$ curve. These relationships are better appreciated by inspection of FIG. 8.

3. Pulse Oximetry waveform ($\Delta SpO_2(t)$): LVET is defined as the temporal interval (seconds) from the onset of the oximetric pulse at zero baseline, signifying the onset of ejection, albeit with a time delay, to the oximetry wave equivalent of the dicrotic notch, which signifies aortic valve closure, albeit with a time delay, and the end of ejection. The oximetry waveform can be obtained from any appropriate site on, or within the human body, but, in the preferred embodiment, the distal digit of the human finger is deemed most appropriate.

4. Applanation Tonometry Pressure Pulse waveform ($\Delta P(t)_{(radial)}$): LVET is defined as the temporal interval (seconds) from the onset of the pressure pulse at zero baseline, signifying the onset of ejection, albeit with a time delay, to the dicrotic notch equivalent, which signifies aortic valve closure, albeit with a time delay, and the end of ejection. In the preferred embodiment, the pressure pulse waveform is obtained from the radial artery at the wrist, but may be obtained from any site on the arm, specifically from either brachial artery.

5. Regression Equations for $T_{lve}$ versus Heart Rate (HR): LVET is determined by Weissler's regression equations: Male: $T_{lve}$=−0.0017·HR+0.413; Female: $T_{lve}$=−0.0016·HR+0.418.

It should be noted that any of the above methods of LVET determinations can be used solely, or in combination with each other (e.g. average multiple LVET determinations, use one or more determinations that appear to produce better results, etc.).

With exemplary $dZ/dt$ waveforms, such as those shown in FIG. 3a, point B and point X are readily distinguishable by one skilled in the art of curve analysis. However, these fiducial landmarks are frequently distorted by motion and ventilation artifacts (especially using the transthoracic approach), as well as by certain disease processes. LVET may be more accurately measured by curve analysis of the pulse oximetry and applanation tonometry waveforms (FIG. 3b), or their first time-derivatives. In one embodiment of the invention, either or both methods may be implemented. Of these techniques, applanation tonometry is most likely to demonstrate a dicrotic notch, and, therefore, is considered the preferred technique. Furthermore, for those skilled in the art of computer waveform analysis, the points coinciding with the beginning and end of ejection can be readily identified from the first time-derivative curves of both the oximetry and applanation tonometry waveforms; namely, $d(SpO_2)/dt$ and $dP/dt_{(radial)}$. In the preferred embodiment, the best method constitutes computer analysis of the first time-derivatives. In another embodiment, regression equations for heart rate versus LVET may be implemented.

Methods for Point B Detection on the dZ/dt Waveform:
1. Methods for determining point B when point X is readily identifiable by one skilled in the art of curve analysis (see FIG. 3a).

Figure 4:
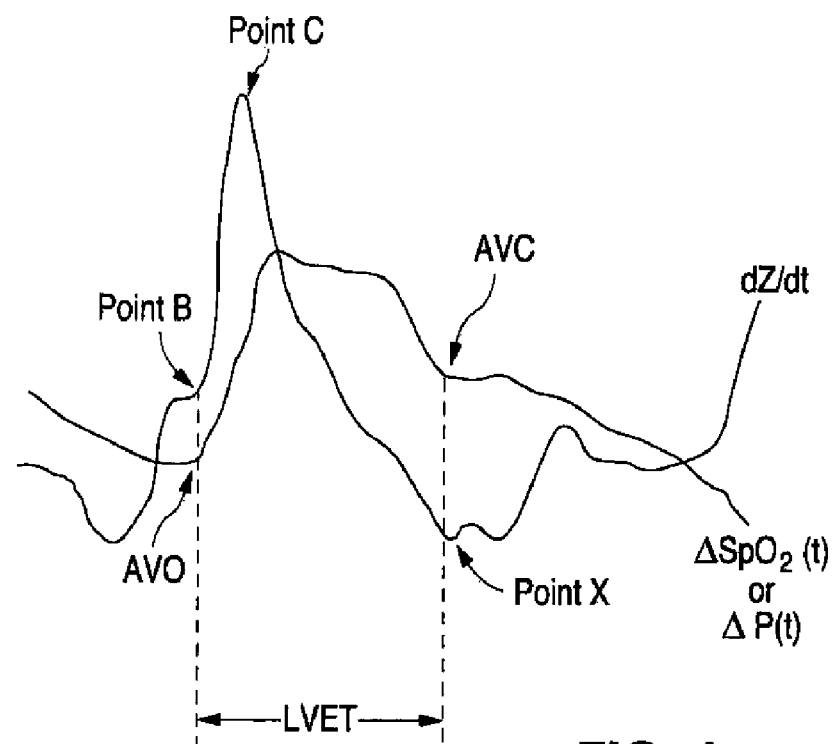
FIG. 4 shows the primary waveforms of $\Delta SpO_2(t)$ and/or $\Delta P(t)$, aligned in time with the dZ/dt waveform.
Figure 5:
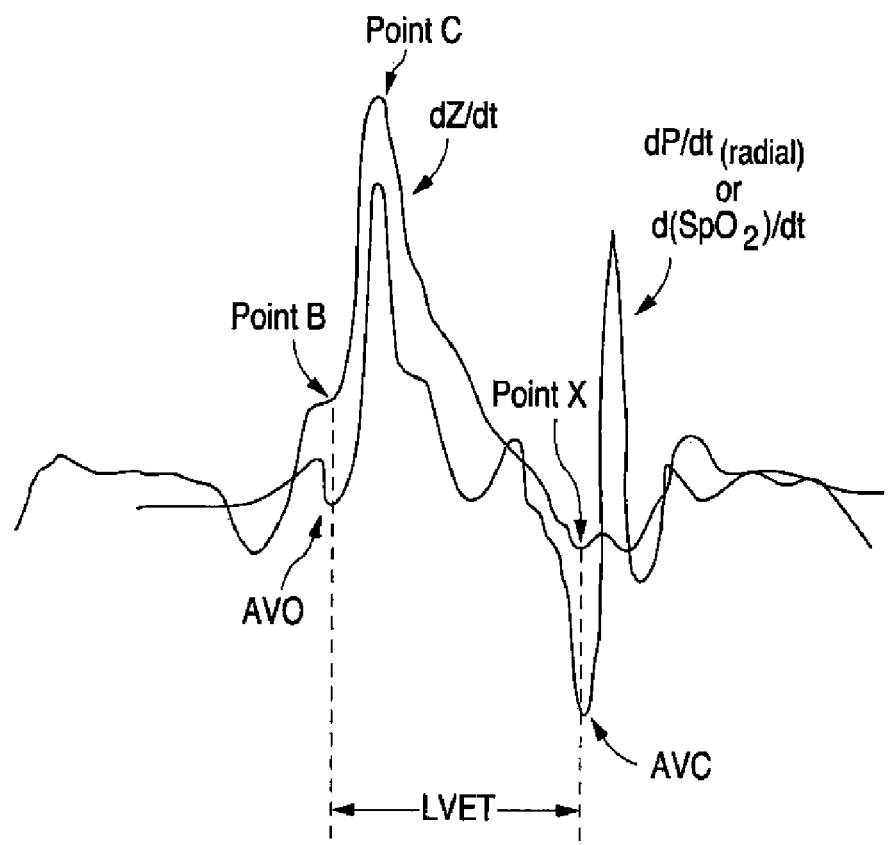
FIG. 5 shows an example where points B and X are distinguishable and that point B corresponds with aortic valve opening (AVO) on the first time-derivatives of either the $\Delta SpO_2(t)$ or $\Delta P(t)$ waveforms and point X corresponds with aortic valve closing (AVC) of either derivative.

Point B on the transbrachial dZ/dt waveform is known to coincide with aortic valve opening, albeit with a time delay. Exemplary dZ/dt waveforms demonstrate a distinct change in slope at, or not uncommonly above the zero baseline impedance, followed by a steep, positive linear segment ending at point C, or $dZ/dt_{max}$. When a distinct change in slope leading to point C is detected at or above the baseline, one skilled in the art of curve analysis can readily identify point B. However, as demonstrated by Debski T T et al. (Biol Psychol 1993; 36:63-74) using the transthoracic method, despite using fiducial landmarks on the time-derivatives of dZ/dt (i.e. $d^2Z/dt^2$ and $d^3Z/dt^3$) to identify this change in slope, detection of point B can be problematic. This inability to correctly identify point B is obvious to those skilled in the art of curve analysis, and especially curve analysis of dZ/dt, by inspection of FIG. 3b. The method disclosed herein provides a new and innovative solution for point B detection. The new method employs one, or a combination of methods disclosed under determination of LVET; namely, $\Delta SpO_2(t)$ and/or $\Delta P(t)_{(radial)}$ (as shown in FIG. 4), or, respectively, their time derivatives, $d(SpO_2)/dt$ and/or $dP/dt_{(radial)}$ (as shown in FIG. 5). The technique of point B detection, as disclosed herein as a preferred embodiment, involves computerized curve fitting and alignment in time of temporal landmark X on the transbrachial dZ/dt curve with the dicrotic notch equivalent of one or both of the measured aforementioned oximetry and pressure curves, and/or preferably with one or both of their first time-derivatives. Independently, or in concert, one or both of the first time-derivative curves can be aligned in time with the transbrachial dZ/dt curve, such that the temporal point of the termination of flow, or aortic valve closure (AVC) equivalent on the first derivative oximetry or pressure curves, can be aligned in time with point X of the transbrachial dZ/dt curve. Point B, coinciding with aortic valve opening (AVO), and the beginning of flow, albeit with a time delay, is identified by determining the temporal point on the transbrachial dZ/dt curve, intersecting, and coinciding in time with the point of onset of flow/pressure on the $\Delta SpO_2(t)/\Delta P(t)$ curves, and/or on their first time-derivatives. This temporal point is identified as a discreet point at the baseline occurring before the first positive maximum upslope measured from foot of the respective baselines of the $\Delta SpO_2(t)$ and/or $\Delta P(t)_{(radial)}$ curves, and/or from their first time-derivatives (FIGS. 3a, 3b, 4, 5, 6).

Figure 6:
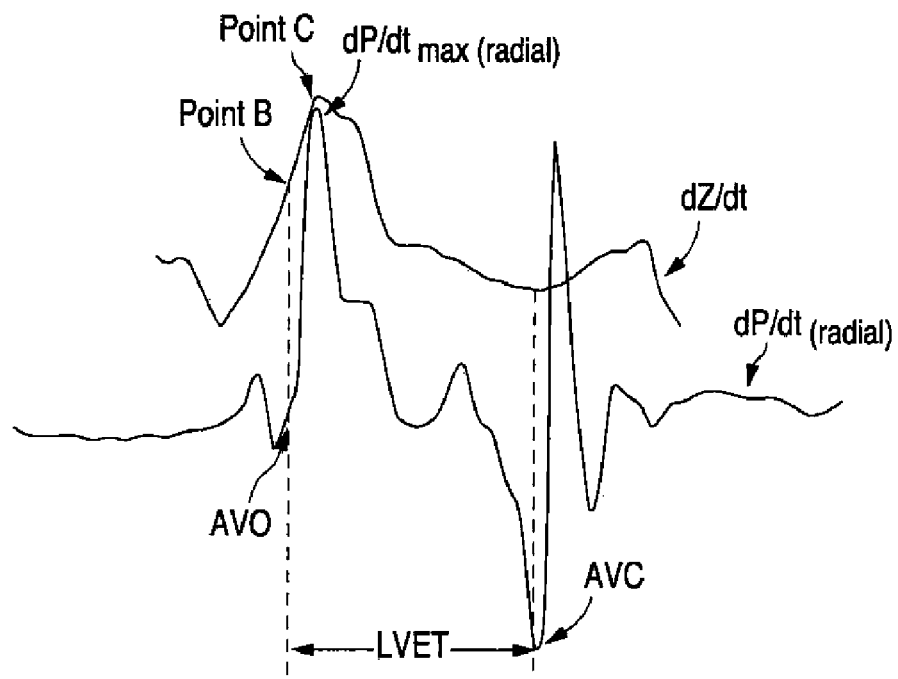
FIG. 6 shows a dZ/dt waveform where points B and X are not distinguishable, and where point C ($dZ/dt_{max}$) is aligned in time with $dP/dt_{max(radial)}$.

2. Method for determining point B when point X is not readily identifiable by one skilled in the art of curve analysis (see FIG. 6):

When point X is not readily identifiable by one skilled in the art of curve analysis, then alternative means must be applied. Requiting alternative means, for example, would be the inability to identify the first zero crossing at baseline impedance after the zero crossing of point C ($dZ/dt_{max}$) on the second time-derivative curve of $\Delta Z(t)$ (i.e., $d^2Z/dt^2$), where said zero crossing corresponds in time to point X and AVC. Said alternative means requires application of the first time-derivative of the applanation tonometry curve, $dP/dt_{(radial)}$ (FIG. 6). For one skilled in the art of curve analysis, said means requires alignment in time of the earliest maximum positive peak of dP/dt ($dP/dt_{max}$) with point C of the transbrachial dZ/dt curve. With point $dP/dt_{max}$ and point C aligned in time, point B can be identified by applying a perpendicular through, and coinciding in time with the onset at baseline of the first positive deflection of dP/dt, where said perpendicular line must intersect the dZ/dt curve at or above baseline impedance. The point of intersection of the perpendicular with the transbrachial dZ/dt curve is designated point B. When the above methods are unavailable, or fail to supply waveforms with fiducial landmarks necessary for point B detection, as assessed by pre-determined criteria, then, as default methods, a point on the transbrachial dZ/dt curve occurring 55 ms prior to point C, but obligatorily at or above baseline impedance, or alternatively, a point 15% above baseline impedance on the dZ/dt curve, is taken as point B.

Method for determining the maximum systolic upslope of transbrachial dZ/dt, otherwise known as transbrachial $d^2Z/dt^2_{max}$: Employing one or a combination of the techniques described herein for point B detection, transbrachial $d^2Z/dt^2_{max}$ is the measured peak positive deflection of the $d^2Z/dt^2$ ($d^2Z/dt^2_{max}$) curve usually occurring temporally proximate point B on the transbrachial dZ/dt curve.

In one embodiment, external calibration of the SV/CO by means of the transbrachial approach:
1. External calibration of $V_{c(brachium)}$ by means of the transthoracic method: Determination of $V_{c(cal)}$.

Because of the high correlation of $dv/dt_{max}$ measured in the aorta with that of the brachial artery, it is claimed that:

$$V_{C(thorax)} = \sqrt[3]{\left[\left(\frac{d^2Z/dt^2_{mean}}{Z_0}\right)_{thorax} \cdot 10^{-2}\right]} \cdot T_{LVE} \quad \text{(equation 2)}$$

$$= V_{C(brachium)} \cdot \sqrt[3]{\left[\left(\frac{d^2Z/dt^2_{mean}}{Z_0}\right)_{transbrachial} \cdot 10^{-2}\right]} \cdot T_{LVE}$$

Since $T_{lve}$ is equivalent for both sides of equation 2, $V_{c(brachium)}$ can be found thusly, $$V_{C(cal)} = V_{C(brachium)} \quad \text{equation 3}$$

$$= \frac{V_{C(thorax)} \sqrt[3]{\left[\left(\frac{d^2Z/dt^2_{mean}}{Z_0}\right)_{thorax} \cdot 10^{-2}\right]}}{\sqrt[3]{\left[\left(\frac{d^2Z/dt^2_{mean}}{Z_0}\right)_{transbrachial} \cdot 10^{-2}\right]}}$$

Where $V_{c(thorax)} = C_{1(thorax)} \cdot [W(kg) \cdot C_2]$ \quad equation 4

Where $0.10 \leq C_{1(thorax)} \leq 0.75$, wherein $C_1 = 0.25$ in the preferred embodiment, Thus, SV by the transbrachial method, externally calibrated from the transthoracic approach is given as, $$SV_{transbrachial} = \quad \text{equation 5}$$

$$V_{C(cal)} + \sqrt[3]{\left[\left(\frac{d^2Z/dt^2_{mean}}{Z_0}\right)_{transbrachial} \cdot 10^{-2}\right]} \cdot T_{LVE}$$

2. Determination of SV from the transbrachial approach by means of auto-calibration: A priori determination of $C_{1(brachium)}$ as a mean value for a population, n.

In order to satisfy the requirements of equation 2, $V_{c(brachium)}$ is found by determining $V_{c(cal)}$ from the solution of equation 3. This operation requires insertion of $V_{c(thorax)}$ as determined from equation 4. Therefore, $V_{c(cal)}$ in equation 3 can be determined thusly;

$$V_{c(cal)} = C_{1(brachium)} \cdot [W(kg) \cdot C_2] \qquad \text{equation 6}$$

Where, $C_1$ is thus, $$C_{1(brachium)} = V_{c(cal)}/[W(kg) \cdot C_2] \qquad \text{equation 7}$$

where, $0 \leq C_1 \leq 50{,}000$, wherein the preferred embodiment $C_1$ is proprietary.

By solving equation 7 for a population, n, determining $V_{c(cal)}$ from equation 3, the mean value of the constant, $C_{1(brachium)}$, can be found for the general population as follows;

$$C_{1(brachium)}(\text{mean}) = [(C_{1\text{-}1} + C_{1\text{-}2} + C_{1\text{-}4} + \ldots C_{1\text{-}n})/n] \qquad \text{equation 8}$$

Where $C_{1(mean)}$ ideally $= C_{1\text{-}1}$ through $C_{1\text{-}n}$. Thus,

SV determination by the transbrachial approach by auto-calibration is given as, $$SV_{transbrachial} = [C_{1(mean, brachial)} \cdot W \cdot C_2] \cdot \sqrt[3]{\left[\left(\frac{d^2Z/dt^2_{mean}}{Z_0}\right)_{transbrachial} \cdot 10^{-2}\right]} \cdot T_{LVE} \qquad \text{equation 9}$$

In another embodiment of the present invention, the SV of the left ventricle can be determined using the transthoracic approach and the mean value of the second time-derivative of the cardiogenically induced transthoracic impedance variation ($\Omega/s^3$). As implemented by inspection of FIG. 7 and related description, a tetrapolar spot electrode array can be applied to a person's body. The description of signal acquisition and processing is precisely that described above with respect to FIG. 2. Stroke volume determination by means of the transthoracic (TT) application is implemented by means of the following equation (where, in the general embodiment, the stroke volume (SV) equation is given as):

$$SV_{TT} = V_{C(TT)} \cdot \sqrt[3]{\left[\left(\frac{d^2Z/dt^2_{mean}}{Z_0}\right)_{TT} \cdot 10^{-2}\right]} \cdot T_{LVE} \qquad \text{equation 10}$$

Where:
$SV_{(TT)}$=stroke volume by the transthoracic approach (mL).
$V_{C(TT)}$=Volume conductor (mL), otherwise known as the volume of electrically participating thoracic tissue ($V_{EPT}$).

$$\text{Ohmic mean velocity}(1/\text{sec}) = \sqrt[3]{\left[\left(\frac{d^2Z/dt^2_{mean}}{Z_0}\right)_{TT} \cdot 10^{-2}\right]} \qquad \text{equation 11}$$

$d^2Z/dt^2_{mean}$ is determined identically as described above with regard to equations 1 and 1a-1g.

$T_{LVE}$=left ventricular ejection time (seconds, sec, s).

Evaluation, ranges and preferred embodiments of the input variables of equation 10 are as follows:

$$V_{C(TT)} = \zeta \cdot (C_2 \cdot W \cdot C_3) \qquad \text{equation 12}$$

$$\zeta(\text{zeta}) = \left(C_1 - C_1 \frac{Z_0}{Z_c} + \frac{Z_0^2}{Z_c^2}\right) (\text{dimensionless})$$

$1.0 \leq C_1 \leq 8.0$, wherein the preferred embodiment $C_1 = 4$.

$Z_0$ (Ohm, $\Omega$)=the transthoracic base impedance, or static D.C. component of the total transthoracic impedance, $Z(t)$.

$Z_c$ ($\Omega$)=the critical level of base impedance; wherein, $15\Omega \leq Z_c \leq 25\Omega$, and wherein the preferred embodiment, $Z_c = 20\Omega$. For all values of $Z_0 < 20\Omega$, $\zeta > 1.0$, and for all values of $Z_0 \geq 20\Omega$, $\zeta = 1.0$.

$0.10 \leq C_2 \leq 0.75$, wherein the preferred embodiment, $C_2 = 0.25$

W=weight in kilograms (kg)

$$C_3 = \frac{C_4}{(BMI_N)^y} = \text{mL/kg} \qquad \text{equation 13}$$

$35 \leq C_4 \leq 100 = \text{mL/kg}$, wherein the preferred embodiment, $C_4 = 70$ mL/kg.

$BMI_N$=normalized body mass index (dimensionless), where $0.5 \leq BMI_N \leq 5.0$, wherein the preferred embodiment $BMI_N = 1.0$.

$BMI_N = BMI_P/C_5$ $BMI_P$=a person's body mass index (W(kg)/H(m$^2$), i.e. kg/m$^2$), where W=a person's weight in kilograms (kg), and H=a person's height in meters (m).

$C_5$=a person's ideal body mass index (kg/m$^2$), where $10 \leq C_5 \leq 100$, wherein the preferred embodiment, $C_5 = 24$ kg/m$^2$.

y is an exponent, $0.25 \leq y \leq 1.0$, wherein the preferred embodiment, y=0.5, where 1/y=equivalent root function, where, $\sqrt[1/y]{BMI_N} = (BMI_N)^y$.

$35 \leq C_3 \leq 100$, wherein the preferred embodiment, $C_3 = 70$ mL/kg.

$$V_{C(TT)}(\text{mL}) = \left[\left(C_1 - C_1 \frac{Z_0}{Z_c} + \frac{Z_0^2}{Z_c^2}\right) \cdot (C_2 \cdot W \cdot C_3)\right] \qquad \text{equation 14}$$

The preferred embodiment the product of $C_2$ and $C_3$ is a constant K, (i.e. $C_2 \cdot C_3 = K$), where $10 \leq C_2 \cdot C_3 \leq 35$, wherein the preferred embodiment, $C_2 \cdot C_3 = 17.5$ mL/kg Where equation 11 in the broadest definition is given as, $$\text{Ohmic mean velocity}(1/\text{sec}) = \sqrt[n_1]{\left[\left(\frac{d^{n_2}Z/dt^{n_2}_{mean}}{Z_0}\right)_{TT} \cdot 10^{-n_3}\right]} \qquad \text{equation 15}$$

$$= \left[\left(\frac{d^{n_2}Z/dt^{n_2}_{mean}}{Z_0}\right)_{TT} \cdot 10^{-n_1}\right]^{n_4}$$

Where:
$1.0 \leq n_1 \leq 10$, wherein the preferred embodiment, $n_1 = 3$.
$1.0 \leq n_2 \leq 10$, wherein the preferred embodiment, $n_2 = 2$.
$0 < n_3 \leq 5$, wherein the preferred embodiment, $n_3 = 2$.
$0.1 \leq n_4 \leq 1.0$, wherein the preferred embodiment, $n_4 = 0.333$.

$$n_4 = \frac{1}{n_1}$$

$T_{LVE}$=left ventricular ejection time (seconds, sec).

Where the stroke volume equation for the transthoracic application in its broadest definition is given as, $$SV_{TT} = \left[\left(C_1 - C_1\frac{Z_0}{Z_c} + \frac{Z_0^2}{Z_c^2}\right) \cdot (C_2 \cdot W \cdot C_3)\right] \cdot$$
$$\sqrt[n_1]{\left[\left(\frac{d^{n_2}Z/dt_{mean}^{n_2}}{Z_0}\right) \cdot 10^{-n_3}\right]} \cdot T_{LVE}$$

equation 16

Wherein as operationally implemented in the preferred embodiment, the stroke volume equation for the transthoracic application is given as, $$SV_{TT} = \left[\left(C_1 - C_1\frac{Z_0}{Z_c} + \frac{Z_0^2}{Z_c^2}\right) \cdot (C_2 \cdot W \cdot C_3)\right] \cdot$$
$$\sqrt[3]{\left[\left(\frac{d^2Z/dt_{mean}^2}{Z_0}\right)_{TT} \cdot 10^{-2}\right]} \cdot T_{LVE}$$

equation 17

It is to be understood that the present invention is not limited to the embodiment(s) described above and illustrated herein, but encompasses any and all variations falling within the scope of the appended claims.

What is claimed is:

1. An apparatus for determining stroke volume by bioimpedance from a patient, comprising:
    two or more spaced apart alternating current flow electrodes positionable on a patient;
    two or more spaced apart voltage sensing electrodes positionable on the patient and between the alternating current flow electrodes;
    an alternating current source electrically connected to the alternating current flow electrodes;
    a voltmeter electrically connected to the voltage sensing electrodes; and
    a processing unit in communication with the voltage sensing electrodes, wherein the processing unit is configured to use a voltage sensed by the voltage sensing electrodes to calculate a cardiogenically induced impedance variation value of the patient, and to determine a stroke volume of the patient by multiplying the cardiogenically induced impedance variation value by a volume conductor $V_C$ and by a left ventricular ejection time $T_{LVE}$;
    wherein the processing unit determines the volume conductor $V_C$ as:

$$V_C = \left(C_1 - C_1\frac{Z_0}{Z_c} + \frac{Z_0^2}{Z_c^2}\right) \cdot (C_2 \cdot W \cdot C_3),$$

where:
    $C_1$ is at least 1.0 and no greater than 8.0,
    $Z_0$ is a transthoracic base impedance or a static D.C. component of a total transthoracic impedance,
    $Z_c$ is a critical level of base impedance that is at least 15Ω and no greater than 25Ω,
    $C_2$ is at least 0.10 and no greater than 0.75,
    W is a kilogram weight of the patient, and
    $C_3$ is at least 35 and no greater than 100.

2. The apparatus of claim 1, wherein the cardiogenically induced impedance variation value is a first or a second time-derivative of a cardiogenically induced impedance variation of the patient.

3. The apparatus of claim 1, wherein the left ventricular ejection time $T_{LVE}$ is obtained from a first time-derivative of the cardiogenically induced impedance variation (dZ/dt) waveform.

4. The apparatus of claim 3, wherein a trigger for initiating processing of the dZ/dt waveform is obtained from an R wave of an antecedent ECG waveform or a peak of an antecedent dZ/dt waveform.

5. The apparatus of claim 1, wherein the left ventricular ejection time $T_{LVE}$ is obtained from a pulse oximetry waveform ($\Delta SpO_2(t)$) or a first time-derivative $dSpO_2(t)/dt$ thereof.

6. The apparatus of claim 1, wherein the left ventricular ejection time $T_{LVE}$ is obtained from an applanation tonometry (pressure) waveform ($\Delta P(t)$) or a first time-derivative $dP(t)/dt$ thereof.

7. The apparatus of claim 1, wherein:
    $C_1$ is substantially 4,
    $Z_c$ is substantially 20Ω,
    $C_2$ is substantially 0.25, and
    $C_3$ is substantially 70.

8. The apparatus of claim 1, wherein:
    for all values of $Z_0$ less than 20Ω, the processing unit determines that $$\left(C_1 - C_1\frac{Z_0}{Z_c} + \frac{Z_0^2}{Z_c^2}\right)$$

is greater than 1.0, and
    for all values of $Z_0$ at least 20Ω, the processing unit determines that $$\left(C_1 - C_1\frac{Z_0}{Z_c} + \frac{Z_0^2}{Z_c^2}\right) \text{ is } 1.0.$$

1.0.

9. The apparatus of claim 1, wherein $C_2$ multiplied by $C_3$ is at least 10 and no greater than 35.

10. The apparatus of claim 9, wherein $C_2$ multiplied by $C_3$ is substantially 17.5 mL/kg.

11. The apparatus of claim 1, wherein:

$$C_3 = \frac{C_4}{(BMI_N)^y} = \text{mL/kg},$$

wherein:
    $C_4$ is at least 35 and no greater than 100,
    $BMI_N$ is a normalized body mass index that is at least 0.5 and no greater than 5.0, and
    y is at least 0.25 and no greater than 1.0.

12. The apparatus of claim 11, wherein:
    $C_4$ is substantially 70 mL/kg,
    $BMI_N$ is substantially 1.0, and
    y is substantially 0.5.

13. The apparatus of claim 12, wherein:

$$BMI_N = \frac{W}{C_5 \cdot H^2}$$

wherein:
H is the patient's height in meters, and
$C_5$ is the patient's ideal body mass index (kg/m²) of at least 10 and no greater than 100.

14. The apparatus of claim 13, wherein $C_5$ is substantially 24 kg/m².

15. A method of determining stroke volume by bioimpedance from a patient, comprising:
positioning two or more spaced apart alternating current flow electrodes on a patient;
positioning two or more spaced apart voltage sensing electrodes on the patient and between the alternating current flow electrodes;
providing an alternating current flow (I(t)) through the electrically conductive electrodes creating a current field;
measuring a voltage (U(t)) between the voltage sensing electrodes within the current field;
calculating a cardiogenically induced impedance variation value of the patient using the measured voltage (U(t));
determining a volume conductor $V_C$ as:

$$V_C = \left(C_1 - C_1 \frac{Z_0}{Z_c} + \frac{Z_0^2}{Z_c^2}\right) \cdot (C_2 \cdot W \cdot C_3),$$

where:
$C_1$ is at least 1.0 and no greater than 8.0,
$Z_0$ is a transthoracic base impedance or a static D.C. component of a total transthoracic impedance,
$Z_c$ is a critical level of base impedance that is at least 15Ω and no greater than 25Ω,
$C_2$ is at least 0.10 and no greater than 0.75,
W is a kilogram weight of the patient, and
$C_3$ is at least 35 and no greater than 100; and
calculating a stroke volume of the patient by multiplying the cardiogenically induced impedance variation value by the volume conductor $V_C$ and by a left ventricular ejection time $T_{LVE}$.

16. The method of claim 15, wherein the cardiogenically induced impedance variation value is a first or a second time-derivative of a cardiogenically induced impedance variation of the patient.

17. The method of claim 15, further comprising:
obtaining the left ventricular ejection time $T_{LVE}$ from a first time-derivative of the cardiogenically induced impedance variation (dZ/dt) waveform.

18. The method of claim 17, wherein a trigger for initiating a processing of the dZ/dt waveform is obtained from an R wave of an antecedent ECG waveform or a peak of an antecedent dZ/dt waveform.

19. The method of claim 15, further comprising:
obtaining the left ventricular ejection time $T_{LVE}$ from a pulse oximetry waveform ($\Delta SpO_2(t)$) or a first time-derivative $dSpO_2(t)/dt$ thereof.

20. The method of claim 15, further comprising:
obtaining the left ventricular ejection time $T_{LVE}$ from an applanation tonometry (pressure) waveform ($\Delta P(t)$) or a first time-derivative dP(t)/dt thereof.

21. The method of claim 15, wherein:
$C_1$ is substantially 4,
$Z_c$ is substantially 20Ω,
$C_2$ is substantially 0.25, and
$C_3$ is substantially 70.

22. The method of claim 15, further comprising:
for all values of $Z_0$ less than 20Ω, determining that $$\left(C_1 - C_1 \frac{Z_0}{Z_c} + \frac{Z_0^2}{Z_c^2}\right)$$

is greater than 1.0, and
for all values of $Z_0$ at least 20Ω, determining that $$\left(C_1 - C_1 \frac{Z_0}{Z_c} + \frac{Z_0^2}{Z_c^2}\right)$$

is 1.0.

23. The method of claim 15, further comprising:
determining $C_2$ multiplied by $C_3$ is at least 10 and no greater than 35.

24. The method of claim 23, wherein $C_2$ multiplied by $C_3$ is substantially 17.5 mL/kg.

25. The method of claim 15, further comprising:
determining that $$C_3 = \frac{C_4}{(BMI_N)^y} = mL/kg,$$

wherein:
$C_4$ is at least 35 and no greater than 100,
$BMI_N$ is a normalized body mass index that is at least 0.5 and no greater than 5.0, and
y is at least 0.25 and no greater than 1.0.

26. The method of claim 25, wherein:
$C_4$ is substantially 70 mL/kg,
$BMI_N$ is substantially 1.0, and
y is substantially 0.5.

27. The method of claim 26, wherein:

$$BMI_N = \frac{W}{C_5 \cdot H^2}$$

wherein:
H is the patient's height in meters, and
$C_5$ is the patient's ideal body mass index (kg/m²) of at least 10 and no greater than 100.

28. The method of claim 27, wherein $C_5$ is substantially 24 kg/m².

* * * * *